United States Patent
Mardiks et al.

(10) Patent No.: US 9,192,325 B2
(45) Date of Patent: Nov. 24, 2015

(54) APPARATUS AND METHOD FOR REAL-TIME MEASUREMENT OF CHANGES IN VOLUME OF BREAST AND OTHER ORGANS

(71) Applicant: MILKOTECH SYSTEMS LTD., Neve Yarak (IL)

(72) Inventors: Eitan Mardiks, Raanana (IL); Gily Netzer, Neve Yarak (IL); David Simeon Blondheim, Mitzpe Netofa (IL)

(73) Assignee: MILKOTECH SYSTEMS LTD, Neve Yarak (IL)

( * ) Notice: Subject to any disclaimer, the term of this patent is extended or adjusted under 35 U.S.C. 154(b) by 0 days.

(21) Appl. No.: 14/613,417

(22) Filed: Feb. 4, 2015

(65) Prior Publication Data

US 2015/0148709 A1    May 28, 2015

Related U.S. Application Data

(63) Continuation of application No. 13/404,991, filed on Feb. 24, 2012, now Pat. No. 8,992,445.

(60) Provisional application No. 61/447,052, filed on Feb. 27, 2011.

(51) Int. Cl.
```
A61B 5/00      (2006.01)
A61B 5/107     (2006.01)
A61B 5/11      (2006.01)
A61M 1/06      (2006.01)
A41C 3/04      (2006.01)
```

(52) U.S. Cl.
CPC .............. *A61B 5/1073* (2013.01); *A61B 5/0053* (2013.01); *A61B 5/11* (2013.01); *A61B 5/4288* (2013.01); *A61B 5/4312* (2013.01); *A61B 5/4878* (2013.01); *A61B 5/6804* (2013.01); *A61B 5/6843* (2013.01); *A61B 5/7278* (2013.01); *A61B 5/742* (2013.01); *A61M 1/062* (2014.02); *A41C 3/04* (2013.01); *A61B 2503/04* (2013.01); *A61M 2205/3389* (2013.01); *A61M 2205/3396* (2013.01)

(58) Field of Classification Search
CPC ...... A61B 5/11; A61B 5/1073; A61B 5/4312; A61B 5/6804
See application file for complete search history.

(56) References Cited

U.S. PATENT DOCUMENTS

| | | | | |
|---|---|---|---|---|
| 5,730,139 | A * | 3/1998 | Miyazaki et al. | 600/493 |
| 6,423,010 | B1 * | 7/2002 | Friedman et al. | 600/494 |
| 6,602,199 | B2 * | 8/2003 | Chen et al. | 600/485 |

(Continued)

*Primary Examiner* — Max Hindenburg
(74) *Attorney, Agent, or Firm* — Daniel J. Swirsky; AlphaPatent Associates Ltd.

(57) ABSTRACT

An apparatus and method for determination of change in volume of a body part or body organ on a real-time basis. In a breastfeeding application, an inflatable cuff is positioned on a nursing breast and allows direct access to the nipple by the breastfeeding infant. The inflatable cuff includes an outer shell portion and an inner inflatable bladder. The pressure in the bladder is monitored regularly by a pressure sensor, during a breastfeeding session. When the pressure drops below a preselected pressure, a controller directs a pump to pump air into the inflatable bladder to maintain the preselected pressure. The volume of added air is monitored during the breastfeeding session. Various calibrations are used to correlate the amount of added air, to the volume of breast milk withdrawn from the breast. The volume of breast milk withdrawn during breastfeeding is calculated and displayed throughout the breastfeeding session.

18 Claims, 7 Drawing Sheets

(56) References Cited

U.S. PATENT DOCUMENTS

| | | | |
|---|---|---|---|
| 7,479,154 B2* | 1/2009 | McEwen et al. | 606/202 |
| 8,206,414 B2* | 6/2012 | Horvat | 606/201 |
| 8,425,426 B2* | 4/2013 | McEwen et al. | 600/490 |
| 8,992,445 B2* | 3/2015 | Blondheim et al. | 600/587 |

* cited by examiner

APPARATUS AND METHOD FOR REAL-TIME MEASUREMENT OF CHANGES IN VOLUME OF BREAST AND OTHER ORGANS

CROSS-REFERENCE TO RELATED APPLICATIONS

The present application is a continuation of U.S. patent application Ser. No. 13/404,991, filed Feb. 24, 2012, and titled "Apparatus and Method for Real-Time Measurement of Changes in Volume of Breast and Other Organs," which claims priority from U.S. Provisional Patent Application No. 61/447,052, filed Feb. 27, 2011 and titled "Device for Measurement of Changes in Volume of Organs," the contents of which is incorporated herein by reference in its entirety.

TECHNICAL FIELD

The disclosure relates to devices and methods for making real-time measurements of changes in volume of organs. More particularly, the disclosure relates to an apparatus and method for monitoring an amount of breast milk withdrawn from a breast by an infant during a breastfeeding session.

BACKGROUND

It is important to monitor the change in volume of an animal's organ over a period of time or during a physiological or other event, or other session.

Breastfeeding is medically important to infants' wellbeing and development. It is important to verify that a sufficient volume of milk is ingested by the infant during the breastfeeding session. A deficiency in natural mother milk requires supplementation. It is useful to monitor the amount of breast milk ingested by an infant on a real-time basis during a breastfeeding session as the volume of milk ingested is indicative of the amount of nutrients ingested by the infant and may indicate the appropriate time to cease the breastfeeding session. Especially with smaller infants, it is important to accurately monitor the volume of milk ingested by the infant during a breastfeeding session.

Ensuring that an infant has ingested a sufficient volume of mother milk is also important for a mother's mental and emotional well-being and to eliminate other issues as potential causes of an infant's uneasiness. For example, if an infant cries for an unknown reason, the mother can more easily identify the cause for crying once the mother has eliminated hunger as a reason for the crying. In addition to a mother's concerns, there are several medical situations where having knowledge about the amount of milk the infant ingests is critical for the infant's development and health, such as with premature babies or infants suffering from growth retardation, diarrhea or other causes for loss of fluids or nutrients.

Direct breastfeeding by an infant develops an emotional and psychological bond between mother and child and is desirable. One method for determining an amount of volume of milk ingested by an infant is to pump the breast milk into bottles where it can be measured accurately and then feeding the infant from the bottle. This method removes the intimacy of direct breastfeeding and requires the use, cleaning and storage of bottles, pumping devices, artificial nipples, heating devices and other associated products.

Availability of a device that is able to measure the amount of milk ingested by an infant by nursing, non-invasively and without interfering with the natural nursing process is highly desirable for mothers and healthcare facilities. It would be desirable to provide an apparatus and system that provides for direct nursing by the infant and which provides immediate and continuous feedback regarding the volume of breast milk withdrawn from the breast and therefore ingested by the infant during the breastfeeding session.

It is also medically important to be able to monitor the change in volume in other organs or other body parts such as may be swollen due to edema or lymphedema.

The disclosure addresses these and other needs.

SUMMARY OF THE DISCLOSURE

According to one aspect, an apparatus for repeatedly measuring an amount of fluid depleted from a body part during a time period, is provided. The apparatus comprises: at least one inflatable cuff with a non-distendable outer shell portion, an inner flexible portion that conforms to the body part, and an opening that receives an exit port of the fluid and allows the fluid to pass therethrough; a pressure sensor that measures pressure in the inflatable cuff repeatedly during the time period; and a pump that pumps air into the inflatable cuff responsive to a change in measured pressure as indicated by the pressure sensor repeatedly during the time period.

According to another aspect, an apparatus for measuring an amount of milk removed from a breast during a breastfeeding session, is provided. The apparatus comprises: a bra having two cups and a strap for securing the bra to a user, at least one of the cups including an inflatable cuff with a non-distendable outer shell, an inner flexible portion that conforms to the breast, and an opening for receiving a nipple therethrough and enabling direct contact between a feeding infant's mouth and the nipple; a pressure sensor that obtains pressure measurements in the inflatable cuff on multiple occasions during the breastfeeding session; a pump that pumps air into the inflatable cuff; a controller that receives the pressure measurements on a real-time basis and repeatedly directs the pump to pump air into the inflatable cuff to maintain a predefined pressure when the pressure measurements indicate a drop in pressure.

According to another aspect, a method for dynamically calculating an amount of milk withdrawn by an infant while directly breastfeeding on a woman's breast, is provided. The method comprises: providing a breastfeeding bra wherein at least one cup of the breastfeeding bra includes an inflatable cuff that comprises a non-distendable outer shell that surrounds an associated breast, an inner flexible portion that faces and conforms to the breast, and an opening for receiving a nipple therein and for providing access to the nipple by the infant's mouth. The method further comprises: positioning the breastfeeding bra on the woman and initiating a breastfeeding session; monitoring pressure in the inflatable cuff on multiple occasions during the breastfeeding session; pumping air into the inflatable cuff to maintain a predefined pressure on multiple occasions during the breastfeeding session; determining an amount of air pumped into the inflatable cuff on multiple occasions during the breastfeeding session; and, converting the amount of air into a volume of milk withdrawn on a real-time basis, during the breastfeeding session.

BRIEF DESCRIPTION OF THE DRAWINGS

The present disclosure is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawing.

DETAILED DESCRIPTION

One embodiment of the disclosure provides an apparatus and method for repeatedly monitoring the volume of milk ingested by an infant while directly breastfeeding from a woman's breast. The disclosure includes a breastfeeding bra apparatus with an opening for the woman's nipple that provides access to the nipple for direct breastfeeding by the infant. The apparatus also includes a pump, pressure sensor, temperature sensor, controller, pressure release valve and other features in various embodiments. The apparatus and method monitor and display the volume of milk ingested by an infant during direct breastfeeding. The apparatus and method can also be used to monitor an accumulation of milk in the mother's breast when not breastfeeding.

In other embodiments, the disclosure provides an apparatus for monitoring the change in volume in other organs or body parts that contain fluids either naturally or through swelling such as edemas resulting from inflammation or other causes or lymphedemas. According to this embodiment, the system of the disclosure provides for maintaining a predetermined pressure about the organ or body part to monitor the inflammatory process.

Figure 1:
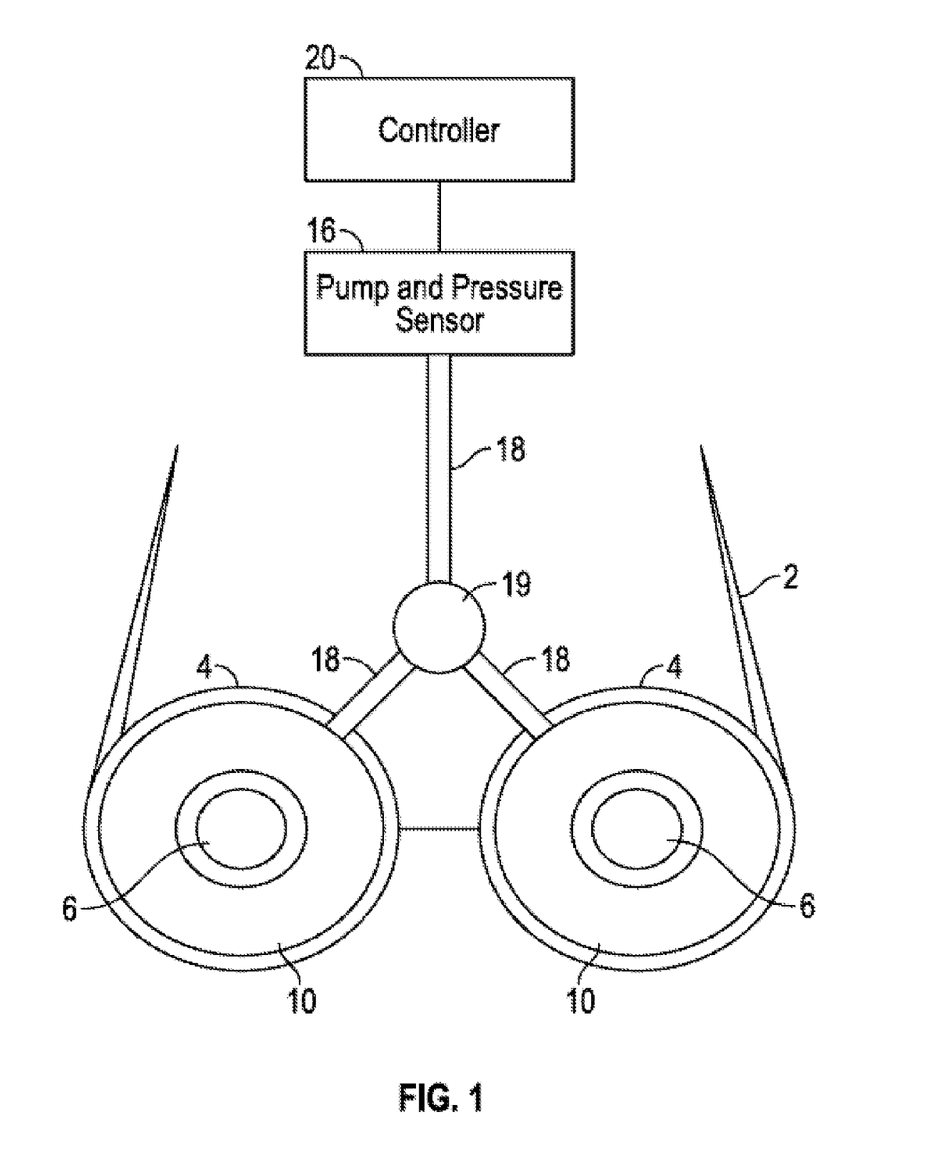
FIG. 1 is a schematic drawing presenting an overview of an embodiment of a breastfeeding apparatus system.

Now turning to the breastfeeding bra apparatus embodiment, FIG. 1 illustrates an embodiment of the breastfeeding apparatus including breastfeeding bra 2 indicated by dashed lines. Breastfeeding bra 2 includes two cups 4, each with a central opening 6. In one embodiment, cups 4 are cone shaped and opening 6 is at the tip of the cone. Opening 6 accommodates an exit port for fluid exiting the body, more particularly for breast milk exiting the body through the nipple in the breastfeeding bra embodiment. Each cup 4 may include an outer cover that covers opening 6 when breastfeeding bra 2 is not being used for breastfeeding as in standard commercially available nursing bras. The outer cover (not shown) may be a flap or other repositionable panel that can be secured in place over opening 6 and then easily removed or repositioned. Each cup 4 includes at least one inflatable cuff 10 that includes an outer shell and an inner flexible liner. The outer shell is formed of a non-deformable, non-distendable material in one embodiment. In one embodiment, each inflatable cuff 10 includes a continuous flexible liner. In another embodiment, inflatable cuff 10 includes an outer shell and multiple discrete inner inflatable portions that are in fluid communication with one another. Breastfeeding bra 2 may come as a single unit in one embodiment. In another embodiment, inflatable cuff 10 is insertible in, and removable from, a commercially available nursing bra. In either embodiment, the inner flexible liner may be in direct contact with the user's breast or there may be a fabric piece interposed between the inner flexible liner of inflatable cuff 10, and the woman's breast. In either case, the inner flexible liner is in a confronting and conformal relationship with the woman's breast.

Pump and pressure sensor unit 16 includes at least one pressure sensor adapted to sense pressure in inflatable cuff 10. Each cup 4 includes an associated inflatable cuff 10 that includes an outer shell and an inner flexible liner. Pump and pressure sensor unit 16 also includes a pump that pumps air into inflatable cuff 10 via tubes 18, responsive to a signal from controller 20 or directly responsive to an indication by the pressure sensor that the pressure in the inflatable cuff 10 of the selected cup, has decreased. Selector 19 directs air flow to the selected cup 4.

Figure 2:
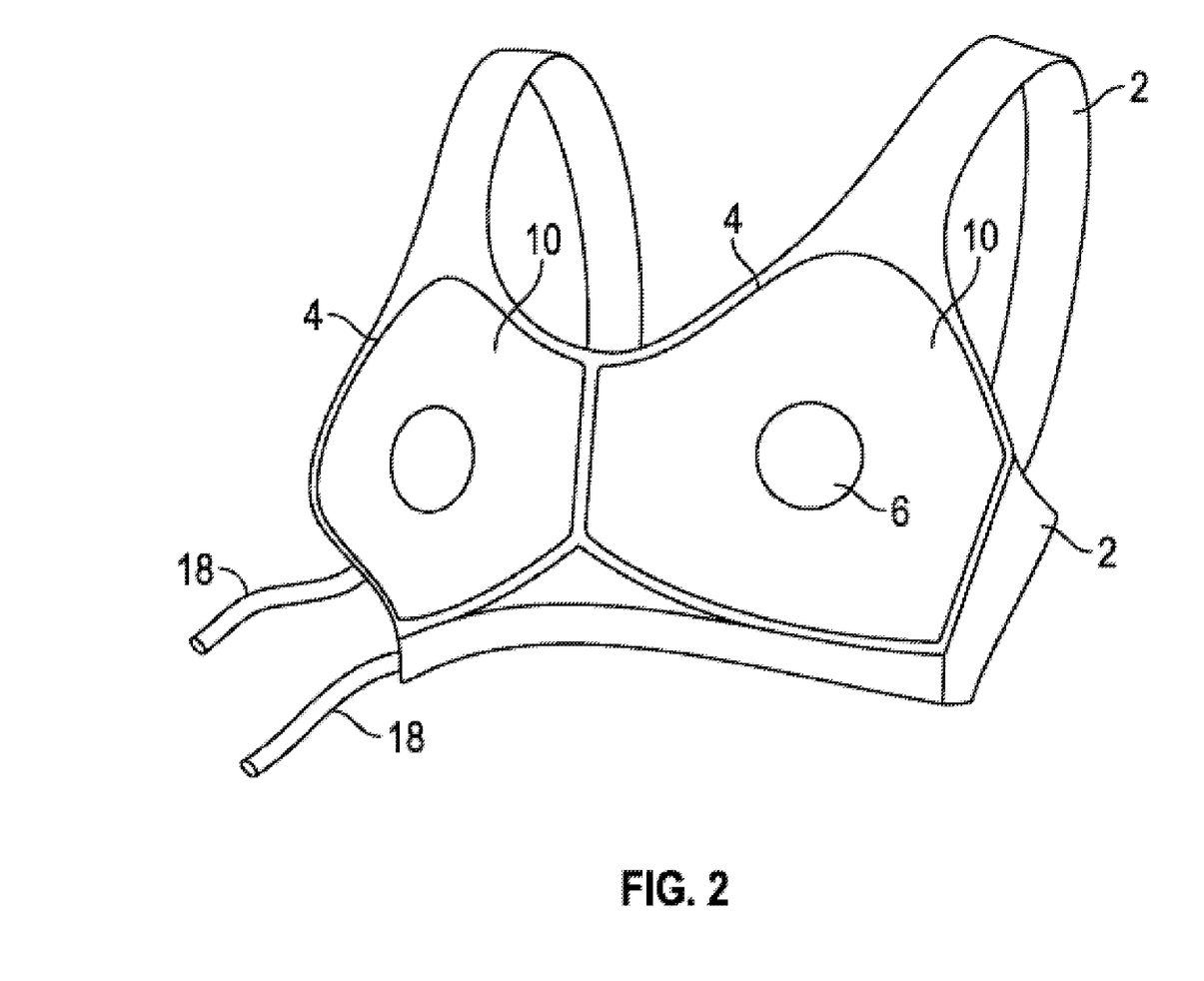
FIG. 2 is a perspective view showing an embodiment of a breastfeeding bra apparatus according to the disclosure.

FIG. 2 is a perspective view showing an embodiment of breastfeeding bra 2. Breastfeeding bra 2 includes two cups 4. Each cup 4 includes inflatable cuff 10 that extends around the breast but includes opening 6. In some embodiments, inflatable cuff 10 completely surrounds the breast with the exception of opening 6. Each inflatable cuff 10 includes an outer shell portion and an inner flexible liner made of a deformable and flaccid material as will be shown in greater detail in the following figures. As such, the cuff is referred to as an inflatable cuff 10. The relative sizes of cup 4, inflatable cuff 10 and opening 6 are exemplary only and will vary in other exemplary embodiments. Breastfeeding bra 2 may be made of materials that are washable, in one embodiment, and may be made of waterproof materials in another embodiment. Breastfeeding bra 2 is reusable. Breastfeeding bra 2 is designed to be lightweight and wearable all day by a woman when not breastfeeding. Inflatable cuff 10 may form part of breastfeeding bra 2 in one embodiment and inflatable cuff 10 is insertible and removable from a nursing bra, in other embodiments.

Figure 3:
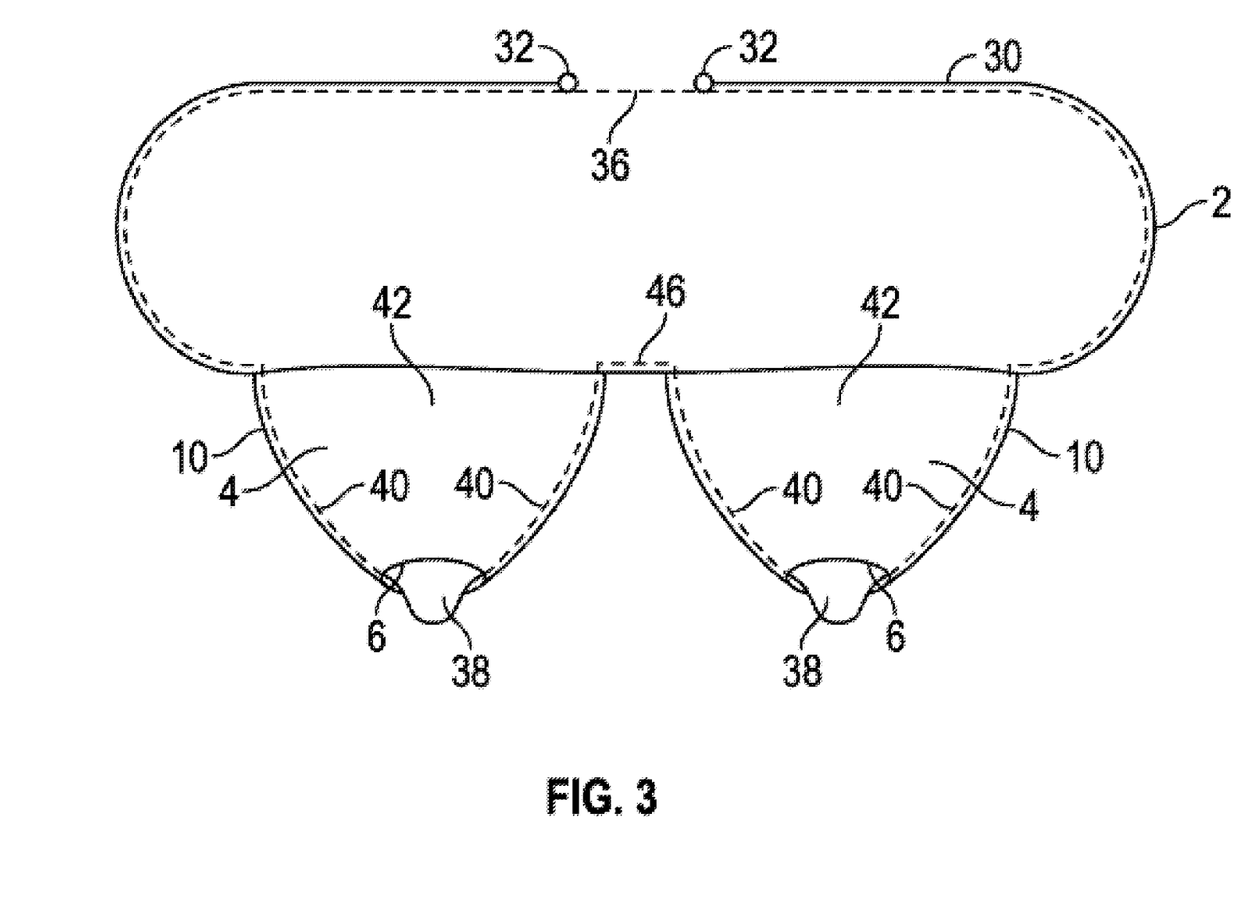
FIG. 3 is a top view of a portion of an embodiment of a breastfeeding bra apparatus according to the disclosure.

FIG. 3 is a top view showing an embodiment of a breastfeeding bra 2. Breastfeeding bra 2 includes two cups 4 with openings 6. Breastfeeding bra 2 includes straps 30 with fasteners 32 for fastening around the user's back 36, indicated by the dashed line. It can be seen that nipples 38 of breast 40 extend through opening 6. Each cup 4 includes inflatable cuff 10 having an outer shell 42 and an inner flexible liner creating an inflatable bladder of sorts. Outer shell 42 extends to chest wall 46 of the wearer when breastfeeding bra 2 is worn by the user and secured by straps 30 and fasteners 32. This ensures that outer shell 42 envelopes breast 40 and remains securely opposed to the chest wall during use.

Breastfeeding bra 2 comes in various sizes, shapes and cup sizes to enable to the above-described fit.

Figure 4:
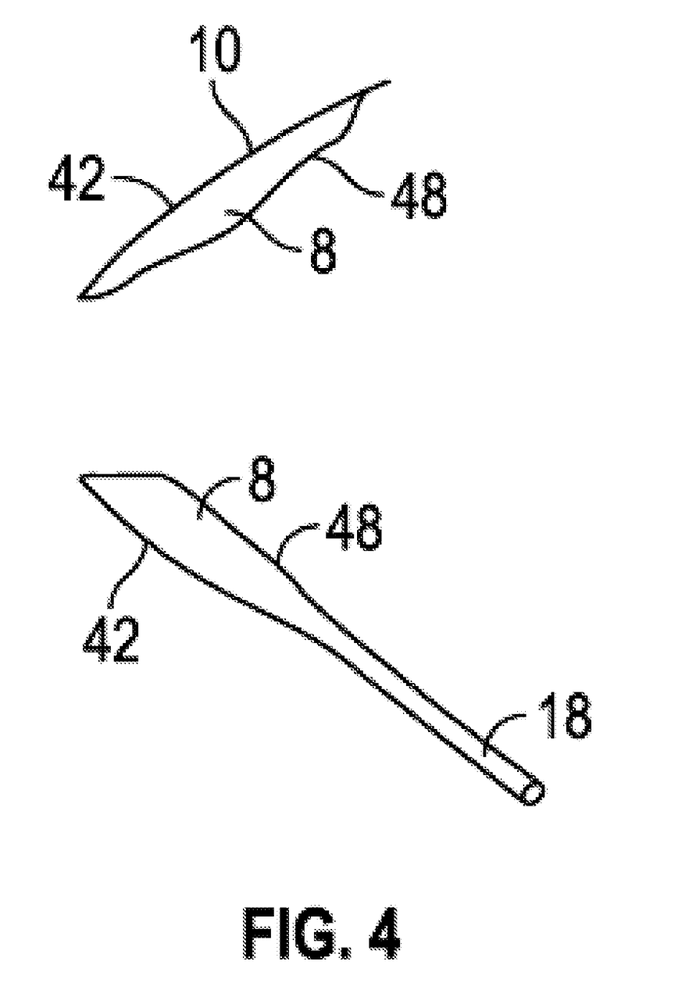
FIG. 4 is a cross-sectional-side view of a portion of an embodiment of an inflatable cuff portion of a breastfeeding bra apparatus according to the disclosure.

FIG. 4 is a cross-sectional side view taken centrally through inflatable cuff 10 and shows portions of inflatable cuff 10 including outer shell 42 and inflated internal portion 8 bounded by inner flexible liner 48. Outer shell 42 is formed of a non-distendable, non-deformable material in one embodiment. In one embodiment, outer shell 42 is formed of a rigid or hard material. Outer shell 42 may be made of plastic or other suitable materials such as a thick layer of rubber, silicone or latex or canvas impregnated with rubber in other embodiments. In various embodiments, outer shell 42 is designed to be more rigid than inner flexible liner 48. Inflatable cuff 10 includes inner flexible liner 48 made of a soft, flexible, flaccid material such as rubber, silicone or other suitable material. Tube 18 connects inflatable cuff 10 to a pump.

Figure 5:
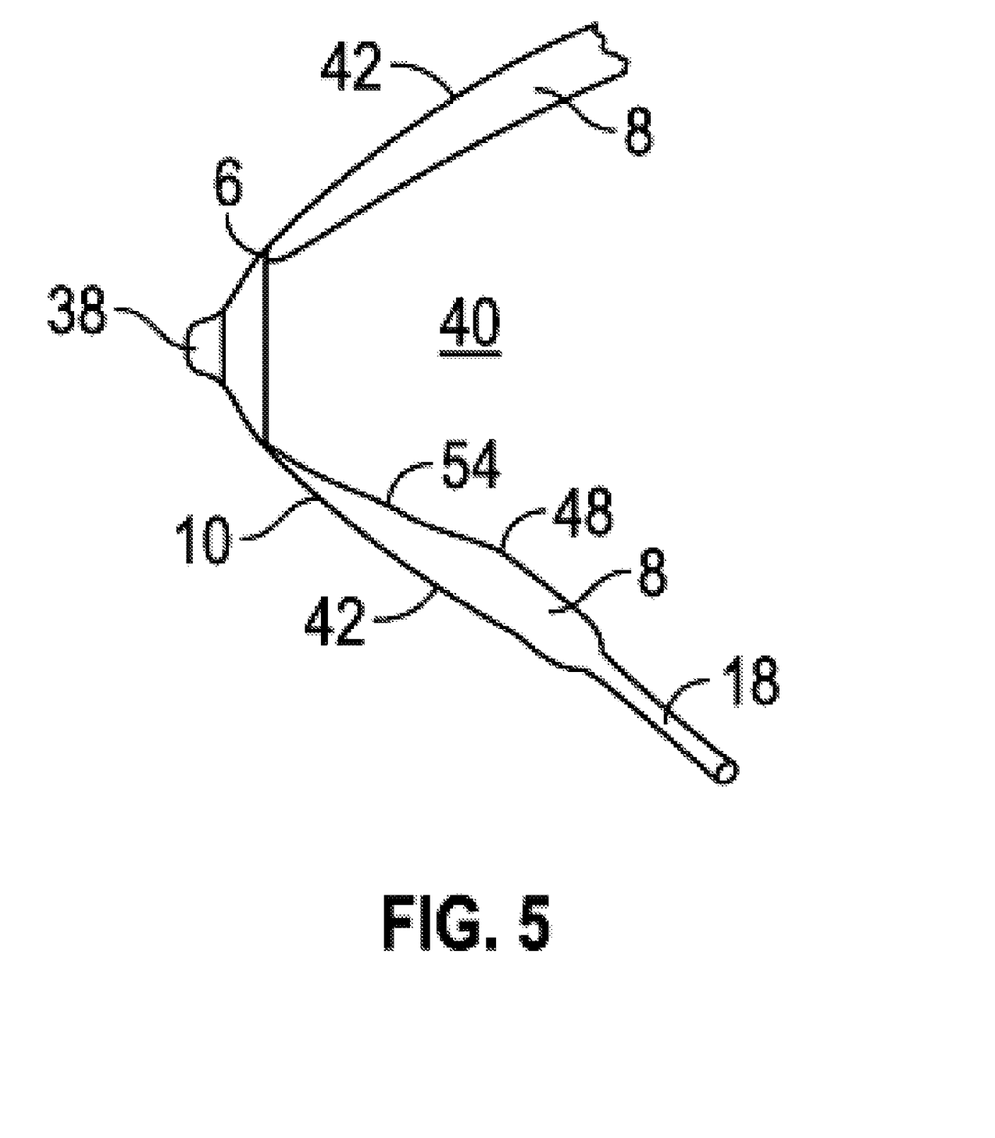
FIG. 5 is a cross-sectional-side view of a portion of an embodiment of an inflatable cuff portion of a breastfeeding bra apparatus, retaining a breast according to the disclosure.

FIG. 5 shows the cuff of FIG. 4 with a breast received therein. Breast 40 is received within inflatable cuff 10 but nipple 38 extends through opening 6 in inflatable cuff 10. This enables direct feeding by an infant. Inner flexible liner 48 of inflatable cuff 10 is in direct contact with surface 54 of breast 40 in one embodiment. In another embodiment, inner flexible liner 48 is separated from surface 54 of breast 40 by a fabric such as an internal portion of breastfeeding bra 2. The interposed fabric is a pliable, soft and comfortable material. In either embodiment, inner flexible liner 48 of inflatable cuff 10 conforms to the contours of breast 40. Inner flexible liner 48 is maintained in direct or indirect but conformal contact with breast surface 54 during feeding. When breast 40 is reduced in size due to the withdrawal of milk through nipple 38, an additional volume of air is introduced through tube 18 to maintain inflatable cuff 10 in conformal relation with breast surface 54. The volume of air added is added until a preselected pressure, such as an initial pressure recorded prior to breastfeeding, is re-attained, as will be discussed below.

Figure 6:
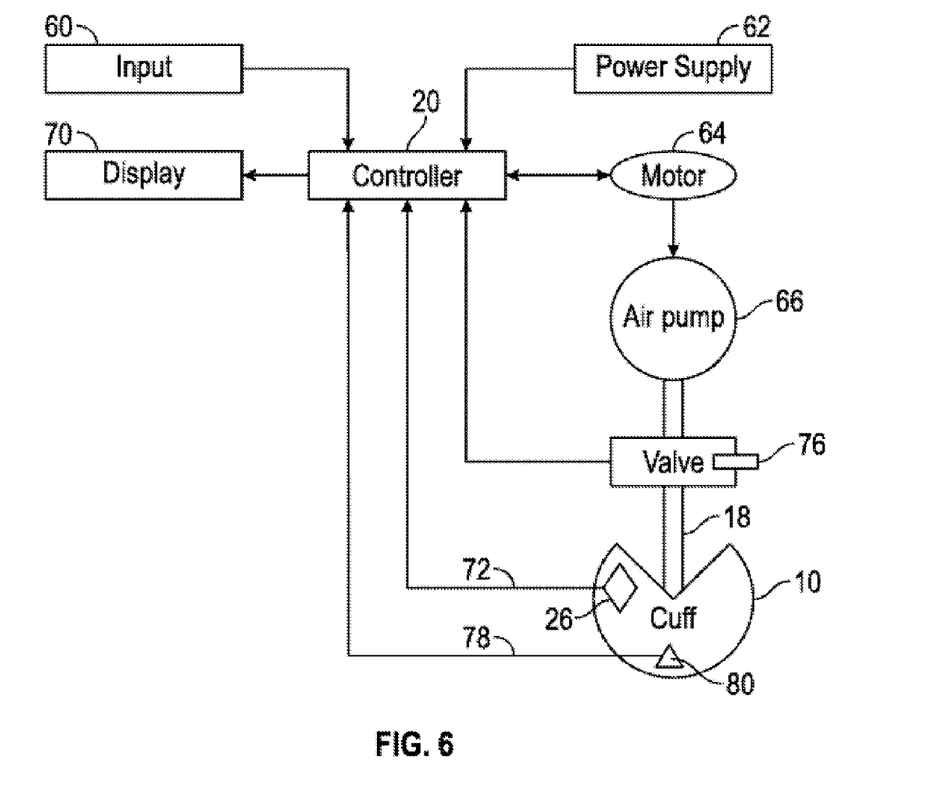
FIG. 6 is a block diagram of an embodiment of an apparatus according to the disclosure.

FIG. 6 is a block diagram that shows one embodiment of the disclosure. Controller 20 is in communication with input device 60 which may be a keypad or other suitable input device. Input device 60 may be used to initiate, pause or terminate the data collecting operation and for various other functions. Data can be collected over discrete and separate portions of the breastfeeding session. For example, the infant may be nursing vigorously during a portion of the breastfeeding session, may then nap for awhile and may feed less vigorously during another period of the breastfeeding session. Data can be collected separately over each of these portions of the breastfeeding session.

Controller 20 is also coupled to power supply 62. Power supply 62 may also be directly or indirectly coupled to other components such as input device 60, motor 64 and air pump 66. In some embodiments, power supply 62 is a battery but various other sources of power are used in other embodiments. Controller 20 is also coupled to display 70. Various display types are used in various embodiments. Controller 20 receives signal 72 from pressure sensor 26 and is in communication with air pump 66. In the illustrated embodiment, controller 20 is in communication with air pump 66 through motor 64, which may be part of air pump 66 in various embodiments. In one embodiment, controller 20, display 70, input device 66, motor 64 and air pump 66 form a single unit which may include a battery power supply 62 in some embodiments. Responsive to signal 72, controller 20 directs the operation of air pump 66 and in the illustrated embodiment, controller 20 controls the operation of motor 64, which may be part of air pump 66 in various embodiments. Controller 20 also receives feedback information from motor 64. In one embodiment, motor 64 is a stepper motor. According to another embodiment, motor 64 is a linear DC motor with a shaft encoder or other means to count the number of motor turns. According to these embodiments, controller 20 can control and monitor the exact number of motor turns at any time. In other embodiments, other types of motors are used to direct air pump 66 to pump air. In one embodiment, motor 64 is directly coupled to air pump 66 or forms part of air pump 66 and each turn of the motor results in a known amount of air pumped by air pump 66 through tube 18 to inflatable cuff 10. In another embodiment, a volume of pumped air is associated with each stroke of air pump 66 or motor 64. Valve 76 is used in some embodiments to release pressure at the end of a breastfeeding session or between different data collection periods during a breastfeeding session or to monitor an accumulation of milk in the breast during non-breastfeeding periods. In some embodiments, air pump 66 is a reversible pump also capable of pumping air out of inflatable cuff 10.

Various electronic controllers may be used as controller 20. In various embodiments, controller 20 may include various processors, microprocessors or other control means.

Controller 20 receives signal 72 indicative of a pressure measurement made by pressure sensor 26 at inflatable cuff 10. More particularly, pressure sensor 26 measures the pressure in the inflatable cuff 10. Pressure sensor 26 measures pressure substantially continuously in one embodiment. Responsive to the pressure measurements, controller 20 directs air pump 66, either directly or through motor 64, to deliver air through tube 18 to inflatable cuff 10 to maintain the predefined pressure, i.e. to restore inflatable cuff 10 to a predefined pressure when pressure sensor 26 records a drop in pressure and this may be done repeatedly during the breastfeeding session. In various embodiments, controller 20 may apply various hysteresis to signal 72 prior to directing air pump 66 to pump air, to correct for various system factors. In one embodiment, signal 78 from temperature sensor 80 is used to correct for air volume differences and pressure measurements associated with different temperatures. According to another embodiment, air pump 66 and motor 64 receive pressure measurement signals directly from pressure sensor 26 and pump air into inflatable cuff 10 responsive to a drop in the pressure in inflatable cuff 10.

According to various embodiments, pressure sensor 26 obtains and delivers pressure measurements at multiple occasions during a breastfeeding session. Pressure sensor 26 may obtain and deliver pressure measurements repeatedly, e.g. periodically, regularly or substantially continuously during a breastfeeding session. In one embodiment, pressure sensor 26 makes pressure measurements multiple times per second and in another embodiment, pressure sensor 26 makes pressure measurements every few seconds, but these are intended to be exemplary only and the frequency of pressure measurements may vary in other embodiments. In one embodiment, pressure sensor 26 generates a voltage that is proportional to the measured pressure and the voltage signal is converted into a digital number using an analog-to-digital (ND) converter within controller 20. Controller 20 monitors the pressure changes, directs air pump 66 to pump additional air into the inflatable cuff 10 to maintain a constant pressure, notes the amount of air added and converts the amount of air added to an associated volume of milk withdrawn according to measures described below.

The volume of milk withdrawn during the entire breastfeeding session or during a portion of the breastfeeding session, or the flow rate of breast milk withdrawn by the infant during the breastfeeding session, is displayed on display 70 in one embodiment. According to other embodiments, controller 20 transmits the results to a computer, mobile phone or any of various other electronic devices that display the results. The transmission may be a wireless or direct transmission. In various embodiments, display 70 is also used for messages to the breastfeeding woman such as "ready," which may indicate that an initial pressure level has been achieved and breastfeeding can begin, see below. In addition to displaying the results, or transmitting the results, controller 20 may also maintain logs of each breastfeeding session. In some embodiments, a tangible computer readable storage medium is used to store the log information.

Various pumps may be used as air pump 66. According to one embodiment, air pump 66 works without a reservoir, i.e. the inlet port of air pump 66 is the environment, i.e. ambient air. This enables air pump 66 to be relatively small in size. Various types of air pumps may be used. In one embodiment, a piezoelectric pump is used. In other embodiments, various other suitable types of pumps can be used. In one embodiment, air pump 66 includes at least one mechanical feature, the movement of which is associated with a particular volume of air pumped. A relationship can be established correlating such movement, e.g. number of rotations of a blade, or number of pump strokes, with a volume of air pumped and a signal of such indication is delivered to controller 20. In various embodiments, air pump 66 is a reversible pump that is additionally capable of pumping air out of inflatable cuff 10.

With reference to the preceding figures, one embodiment of a method for breastfeeding using the described breastfeeding apparatus is as follows. The breastfeeding apparatus includes breastfeeding bra 2 worn by the nursing woman. Openings 6 enable the breastfeeding infant direct access to the breast milk through the woman's nipple which is exposed in opening 6. Immediately preceding a breastfeeding session, the system is turned on and the left or right breast selected. Controller 20 sends a signal to air pump 66 and air pump 66 pumps air through tube 18 to the selected breast, more particularly to the associated inflatable cuff, pressurizing the inflatable cuff to an initial pressure. With outer shell 42 of cup 4 extending to the woman's chest wall, outer shell 42 encompasses the entire breast excluding the nipple and remains in fixed position, secured by straps 30 and fasteners 32 or other means.

When inflatable cuff 10 is inflated to the initial pressure, it occupies a volume between outer shell 42 and breast 40. The pressure may be adjusted statically or dynamically as necessary to achieve the best measurement accuracy and to minimize noise level. The inner flaccid portion, i.e. inner flexible liner 48 of inflatable cuff 10, contacts breast 40. When the pressure stabilizes, breastfeeding can begin. When the infant nurses and milk is extracted through the nipple, the volume of the breast is reduced and the air pressure in inflatable cuff 10 is reduced as inner flexible liner 48 of inflatable cuff 10 loses contact with the shrinking, i.e. depleted breast 40 as outer shell 42 does not deform. Responsive to an indication in a reduction of the internal pressure in inflatable cuff 10 which may be done repeatedly during the breastfeeding session, controller 20 directs air pump 66 to deliver air to inflatable cuff 10. Air is pumped into inflatable cuff 10 until a predefined pressure is achieved as noted by pressure sensor 26. In some embodiments, the predefined pressure is the initial pressure. The amount of air that flows into the inflatable cuffs in order to re-attain the predefined pressure, i.e. maintain a constant pressure, is noted by the controller 20.

In one embodiment, controller 20 calculates the difference between the initial and final volumes in the inflatable cuff 10 by measuring the amount of air added to the inflatable cuff 10. In another embodiment, controller 20 calculates the volume of air added to inflatable cuff 10 in real time or regularly, periodically or continuously during the breastfeeding session. In one embodiment, controller 20 monitors the amount of turns of a component of motor 64 or pump strokes, and uses a correlation or other transformation or conversion function, to determine the amount of air added to inflatable cuff 10. The amount of air added to the inflatable cuff to return to the initial pressure is converted into a volume of milk extracted from the breast using various conversion means including a calibration equation. Similarly, the amount of air added to the inflatable cuffs in time can be converted into a flow rate of milk extracted from the breast during any interval during the breastfeeding session.

The difference in the air volume in the inflatable cuff before and after a measurement increment during a breastfeeding session is typically proportional to the difference in breast volume i.e. the volume of milk extracted by the nursing infant. The amount of air volume added to the inflatable cuff to maintain the initial pressure is typically proportional to the degree of depletion of breast volume i.e. the volume of milk extracted by the nursing infant. The air volume added to the cuff is related to the volume of the milk extracted from the breast. In one embodiment, the relationship can be expressed as: $M=K*(\Delta V)$, where M is the milk volume consumed by the infant and $\Delta V$ is the change in volume, the volume of air added during a data collection period such as a breastfeeding session or part of a breastfeeding session. In one embodiment, $\Delta V=V1-V2$ where V1 and V2 are the air volumes in the inflatable cuff 10 measured before and after a measurement period during nursing, respectively. In one embodiment, $\Delta V$ represents the volume of air pumped as noted by monitoring the pump. K is a constant determined during calibration.

In another embodiment, the volume of breast milk extracted can be attained using a conversion function directly related to a mechanical aspect of the pump or associated motor, such as the number of strokes of the pump. According to this embodiment, the relationship can be expressed as: $M=C*(\#strokes)$, where C is a constant determined during calibration. In another embodiment in which the pump pumps from a fixed reservoir, the amount of air pumped into the inflatable cuff is calculated from the difference between the initial and final volume in the reservoir container of air. In other embodiments, other correlations between volume of air added and breast milk volume, are used. The calculation for determining milk volume may be further adjusted by compensating for environmental changes such as changes in the air temperature in the inflatable cuffs, such as may be indicated by temperature sensor 80 installed in or near inflatable cuff 10. The correlation between air pressure and volume is adjusted by temperature changes.

This procedure is carried out on a real-time basis and the amount of milk withdrawn from the breast, i.e., ingested by the infant, is calculated and displayed at repeatedly, i.e. at various frequencies, periodically, or essentially continuously. According to one embodiment, the amount of milk withdrawn may be presented as a flow rate, i.e., volume of milk withdrawn per time interval.

An on/off switch or other input device may be utilized to communicate with the controller to separately monitor separate time intervals during the overall breastfeeding cycle. According to one embodiment, when the infant is nursing, the apparatus and method provide for indicating the volume of milk ingested during the entire breastfeeding session. According to another embodiment, the breastfeeding session is broken into more than one data collecting period. Further, if the infant ceases breastfeeding for a time, e.g., falls asleep, the system and apparatus can be paused or used to note the accumulation of milk in the breast as indicated by a change in pressure.

According to this milk accumulation embodiment, the volume of the breast increases and exerts a greater pressure upon the inflatable cuff and this increase in pressure can be used to calculate the increase in volume of the breast, i.e., the volume of breast milk accumulated during that period. According to one embodiment, controller 20 may communicate with valve 76 and direct valve 76 to release air pressure by allowing a volume of air to flow through the valve to maintain a predefined pressure. According to this embodiment, the volume of air flowing through valve 76 can be correlated to an increase in breast volume and milk accumulation such as using one of the previous correlation equations, or other methods. In another embodiment, controller 20 may communicate with air pump 66 and direct air pump 66 to pump a volume of air out of inflatable cuff 10 in order to restore inflatable cuff 10 to the predefined pressure. In this embodiment, a correlation between a mechanical aspect of the pump such as number of strokes of the pump, and volume of air, can again be used to determine the increase in volume of milk in the breast. In another embodiment, with no air expelled through valve 36, a correlation can be obtained between an increase of pressure in inflatable cuff 10 and the volume of the breast. According to this embodiment, the increase in volume of the breast during an accumulation period can be calculated. As will be seen, this principle can be applied to other body organs. When the breastfeeding continues, a suitable input device can again be used to initiate a cycle that will indicate the amount of volume ingested by the infant since resuming the breastfeeding session, and/or the cumulative volume since initiation of the breastfeeding session.

Figure 7:
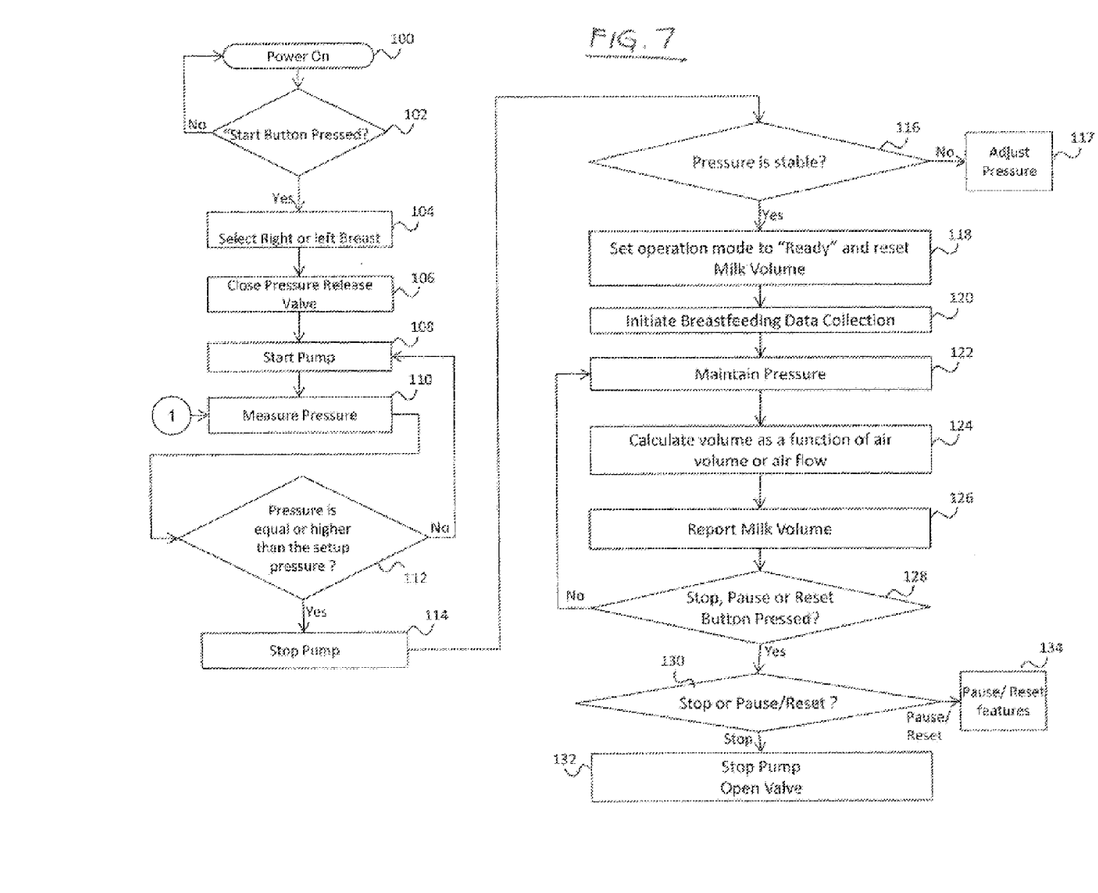
FIG. 7 is a flowchart of an embodiment of a method of the disclosure.

FIG. 7 is a flowchart showing an embodiment of the disclosure. At step 100, the apparatus is powered on. In one embodiment, the apparatus performs a general system initialization and waits for a start button to be activated. At step 102, if the start button is activated, step 104 provides for selecting the right or left breast. The start button and selection of right or left breast may be carried out using input device 60 shown in FIG. 7. At step 106, a pressure release valve such as valve 76 is closed and at step 108, the pump, e.g. air pump 66, is started. At step 110, the pressure sensor measures pressure in inflatable cuff 10 and controller 20 monitors the measured air pressure.

At step 112, the controller compares the pressure to a predefined pressure, also referred to as the setup pressure. If the pressure is equal to or higher than the setup pressure, air pump 66 and any associated motors such as motor 64 is stopped at step 114. A stabilization time may follow during which the controller continues to monitor pressure. If the pressure drops below the predefined, setup pressure, the motor and pump may be turned on to return the pressure in the inflatable cuffs to the setup, predefined pressure at pressure adjust step 117. If the pressure exceeds the setup, predefined pressure, valve 76 may be used to release pressure or the new pressure can be substituted and used as the initial pressure to be maintained throughout the breastfeeding operation. If the pressure is stable at step 116, the initial pressure is recorded and operation mode is set to ready. A message may be displayed indicating that the system is ready. The milk volume calculation is reset. According to the embodiment in which milk volume is calculated based on a number of turns of a component of a motor or pump, the motor cycle counter is reset to zero.

At step 120, the breastfeeding session data collection is initiated such as by pressing a button to initiate a data collection time period. Once breastfeeding begins, step 122 provides for maintaining pressure in the inflatable cuff. This is performed repeatedly during a breastfeeding session in various embodiments. This is performed in one embodiment by activating the pump when the measured pressure drops below a predefined level and stopping the pump when the pressure achieves the predefined level, such as an initial pressure or setup pressure attained in the inflatable cuff before the breastfeeding session began. At step 124, volume of milk is calculated as a function of air volume or air flow in one embodiment. In another embodiment, the volume is a function of number of strokes of air pump 66 or number of motor cycles in the motor that powers air pump 66. According to other embodiments, other techniques for quantifying the volume of air delivered and correlating the volume of air to a volume of milk ingested by the infant, are used.

At step 126, the calculated milk volume is reported such as on display 70 or transmitted to another device. This may be done repeatedly, periodically, regularly, or substantially continuously in various embodiments. In some embodiments, the volume of milk may only be reported after a session has been stopped, such as by stopping the data collection for the breastfeeding session such as at step 128. At step 128, if the stop, pause or reset button is pressed, data collection stops. It is determined at step 130 whether the stop button has been activated. If the stop button has been pressed, indicating a termination of the breastfeeding session, step 132 provides for stopping the pump and opening the valve, such as valve 76, to relieve pressure from inflatable cuff 10.

A pause or reset button may be pressed to indicate that it is desired to terminate data collection for a portion of the breastfeeding session. This may be done if the infant temporarily stops nursing or for various other reasons. After the pause or reset button is activated at step 130 and data collection has ceased, the disclosure provides for various subsequent actions identified as pause/reset features 134. In one embodiment, the reset button causes the termination of an initial data collection period but requests data collection to continue. According to this embodiment, the volumes of milk calculated before and after the reset step may be separately reported. According to one embodiment, data collection continues under the same conditions at which the data collection was stopped. In other words, the data collection is simply reported over separate time periods.

According to the embodiment in which the pause feature is selected, the system stops monitoring the pressure and the pump is not activated. When the pause period is canceled, the system is restarted and returns to the predefined pressure. The changes in air volume of the inflatable cuff necessary to attain the predefined pressure upon restart, are noted. According to the embodiment in which pressure is increased during the pause period, an increase in volume of the breast during this accumulation period is indicated. The volume of milk accumulated during the accumulation period can be determined by using valve 76 to release pressure in the inflatable cuff until the pressure is returned to the predefined pressure. In one embodiment, the volume of milk is calculated using a predetermined correlation between the volume of air passing through valve 76 and volume of milk. In another embodiment, a direct correlation between increased pressure in inflatable cuff and volume of milk is used. In another embodiment, in which air pump 66 is used to pump a volume of air out of inflatable cuff 10 in order to restore inflatable cuff 10 to the predefined pressure. In this embodiment, a correlation between a mechanical aspect of the pump such as number of strokes of the pump, and volume of air can be used to determine the increase in volume of milk in the breast.

According to the aforementioned methods for calculating the volume of breast milk withdrawn, controller 20 may apply signal processing methods such as digital filtering, fast Fourier transforms or other suitable mathematical operations to remove noise and correct for other artifacts such as movements of the nursing woman or the infant.

According to another breastfeeding embodiment in which a change in the volume of a woman's breast is measured, instead of each bra cup including a single inflatable cuff, in another embodiment, there are two or more concentric inflatable cuffs associated with each cup. Each of the concentric inflatable cuffs includes an associated outer shell and inner flexible portion. In one embodiment, the concentric inflatable cuffs are in fluid communication with one another so that air pressure between the two concentric inflatable cuffs becomes equalized. In another embodiment, each of the concentric inflatable cuffs is separately and individually monitored, i.e. using separate pressure sensing systems, according to the aforementioned embodiments.

According to other embodiments, the apparatus and method for monitoring a change in volume in body organs may be used to determine the volume of edema fluid, for determination of lymphedema fluid volume and for determination of post-trauma edema in body extremities. To determine the volume of edema a cuff in the shape of an extremity is connected to a control device which works on the foregoing principles described above, to obtain a predetermined pressure, in the cuff, in one embodiment. The amount of air pumped into the cuff to maintain the pressure is proportional to the amount of edema fluid extracted. As with the embodiment for monitoring the change in breast volume, the cuffs designed for the extremities include an outer shell formed of a non-distendable, non-deformable material and an inner inflatable bladder. The cuff is inflated at baseline to a predetermined pressure, the amount of air needed to reach and maintain this pressure is recorded and then the cuff is deflated. Repeated measurements are performed from time to time (for example daily or before taking the next dose of the diuretic) and the difference between the air added to the system to maintain its predetermined pressure multiplied by a constant, represents the amount of fluid extracted from the extremity since baseline. In other embodiments, the cuff may be designed, sized and shaped for use with other extremities.

For determination of post trauma edema a cuff built to fit an arm or a leg depending on the location of the trauma is inflated to a predetermined pressure. This may be done shortly after the trauma or preferably, as in cases of planned surgery, e.g. knee replacement, before the planned trauma and the amount of air needed to maintain this pressure is recorded and the cuff is then deflated. The cuff can be inflated from time to time when clinically necessary or daily to the same predetermined pressure. The difference between the amounts of air needed to reach the predetermined pressure at baseline versus the subsequent measurements is proportional to the amount of inflammation of the tissues at the time of measurement. When the air needed to reach the predetermined pressure returns to that needed at baseline, the extremity is cured from significant inflammation.

The preceding merely illustrates the principles of the disclosure. It will thus be appreciated that those skilled in the art will be able to devise various arrangements which, although not explicitly described or shown herein, embody the principles of the disclosure and are included within its spirit and scope. Furthermore, all examples and conditional language recited herein are principally intended expressly to be only for pedagogical purposes and to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Although the disclosure has been described in terms of exemplary embodiments, it is not limited thereto. Rather, the appended claims should be construed broadly, to include other variants and embodiments of the disclosure, which may be made by those skilled in the art without departing from the scope and range of equivalents of the disclosure.

What is claimed is:

1. An apparatus comprising:
   at least one cuff, said cuff comprising an inflatable inner portion conforming to a body part;
   a pressure sensor operative to measure pressure in said inflatable cuff repeatedly during a time-period;
   a pump operative to pump a filling-fluid into said inflatable cuff; and
   a controller operative to monitor said pressure sensor, and to control said pump;
   wherein, during said time-period, said controller is operative to:
   repeatedly monitor pressure as indicated by said pressure sensor,
   repeatedly control said pump to maintain constant pressure in said inflatable cuff;
   repeatedly determine an amount of said filling-fluid pumped into said inflatable cuff to maintain said constant pressure,
   repeatedly convert said amount of filling-fluid to a volume of body-fluid depleted from said body part during said time-period, and
   repeatedly provide in real-time to a display an accumulated amount of said body-fluid being depleted from said body part.

2. The apparatus according to claim 1 additionally comprising:
   an opening in said cuff configured to allow said body-fluid depleted from said body part to pass there-through.

3. The apparatus as in claim 1, wherein said controller provides a signal to said pump, and applies hysteresis to said signal.

4. The apparatus as in claim 1, wherein said body part comprises an edematous extremity, and said pressure sensor makes pressure measurements at least at the beginning of said time-period and at intervals during said time-period.

5. The apparatus as in claim 1, wherein said controller further provides real-time indications of a flow rate of said body-fluid being depleted from said body part.

6. The apparatus as in claim 1, wherein said pump is associated with a motor and said controller determines said amount of filling-fluid pumped into said inflatable cuff using a correlation between a volume of filling-fluid pumped by said pump and a number of strokes of said pump.

7. The apparatus as in claim 1, wherein said filling-fluid is ambient air and wherein said pump includes an intake port that receives said ambient air.

8. The apparatus as in claim 1 additionally comprising:
   pressure release mechanism operative to release said filling-fluid from said inflatable portion of said cuff; and wherein said controller is additionally operative to convert a measurement of a volume of said released filling-fluid into a volume of body-fluid accumulated during said time-period.

9. A method for measuring body-fluid depleted from a body part, the method comprising:
   attaching at least one cuff to said body part, said cuff comprising an inflatable inner portion conforming to said body part;
   repeatedly monitoring pressure in said inflatable cuff during a time-period;
   maintaining constant pressure in said inflatable cuff, responsive to said monitoring of said pressure, by repeatedly controlling a pump, said pump operative to pump a filling-fluid into said inflatable cuff;
   repeatedly determining an amount of said filling-fluid pumped into said inflatable cuff to maintain said constant pressure;
   repeatedly converting said amount of said filling-fluid to volume of said body-fluid depleted from said body part during said time-period, and
   repeatedly providing to a display, in real-time, during said time-period, an accumulated amount of said body-fluid being depleted from said body part.

10. The method according to claim 9 additionally comprising:
    providing an opening in said cuff configured to allow said body-fluid depleted from said body part to pass therethrough.

11. The method according to claim 9 additionally comprising:
    providing a signal to said pump, and applying hysteresis to said signal.

12. The method according to claim 9 additionally comprising:
    repeatedly providing real-time indications of flow rate of said body-fluid being depleted from said body part during said time-period.

13. The method according to claim 9 additionally comprising:
    monitoring strokes of a motor associated with said pump to determine said amount of filling-fluid pumped into said inflatable cuff using a correlation between volume of said filling-fluid pumped by said pump and number of strokes of said pump.

14. The method according to claim 9 additionally comprising:
    wherein said inflatable portion of said cuff comprises a plurality of discrete inflatable portions.

15. The method according to claim 9, wherein said filling-fluid is ambient air, and wherein said pump includes an intake port that receives said ambient air.

16. The method according to claim 9, wherein said pump is operative to pumping said filling-fluid out of said inflatable cuff.

17. The method according to claim 9 additionally comprising:
    releasing said filling-fluid from said inflatable portion of said cuff; and
    converting a measurement of a volume of said released filling-fluid into a volume of body-fluid accumulated during said time-period.

18. A controller comprising:
    a connection for controlling a pump operative to pump a filling-fluid into at least one inflatable cuff conforming to a body part; and
    a connection for receiving pressure measurements from a pressure sensor operative to measure pressure in said inflatable cuff during a time-period;
    wherein said controller, repeatedly during said time-period, directs said pump to pump an amount of said filling-fluid into said inflatable cuff to maintain a predefined pressure therein responsive to said pressure measurements;
    wherein said controller, repeatedly during said time-period, converts in real-time said amount of said filling-fluid to a volume of body-fluid depleted from said body part; and
    wherein said controller, repeatedly during said time-period, provides in real-time to a display device at least one of:
    amount of said body-fluid being depleted from said body part,
    flow rate of said body-fluid being depleted from said body part, and
    amount of said body-fluid being accumulated into said body part.

* * * * *